US011000843B2

(12) United States Patent
Doosa et al.

(10) Patent No.: US 11,000,843 B2
(45) Date of Patent: May 11, 2021

(54) CATALYST COMPOSITION FOR CONVERSION OF ALKANES TO ALKENES AND METHOD OF PREPARATION THEREOF

(71) Applicant: INDIAN OIL CORPORATION LIMITED, Mumbai (IN)

(72) Inventors: Hima Bindu Doosa, Faridabad (IN); Ram Mohan Thakur, Faridabad (IN); Vineeth Venu Nath, Faridabad (IN); Eswar Prasad Dalai, Faridabad (IN); Debasis Bhattacharyya, Faridabad (IN); Sanjiv Kumar Mazumdar, Faridabad (IN); Sankara Sri Venkata Ramakumar, Faridabad (IN)

(73) Assignee: INDIAN OIL CORPORATION LIMITED, Mumbai (IN)

(*) Notice: Subject to any disclaimer, the term of this patent is extended or adjusted under 35 U.S.C. 154(b) by 0 days.

(21) Appl. No.: 16/262,722

(22) Filed: Jan. 30, 2019

(65) Prior Publication Data
US 2019/0262821 A1 Aug. 29, 2019

(30) Foreign Application Priority Data

Feb. 27, 2018 (IN) .............................. 201821007391

(51) Int. Cl.
B01J 38/68 (2006.01)
B01J 23/847 (2006.01)
B01J 23/22 (2006.01)
B01J 23/86 (2006.01)
B01J 23/26 (2006.01)
B01J 23/94 (2006.01)
B01J 38/02 (2006.01)
C07C 5/42 (2006.01)
B01J 23/92 (2006.01)

(52) U.S. Cl.
CPC .............. B01J 38/68 (2013.01); B01J 23/22 (2013.01); B01J 23/26 (2013.01); B01J 23/8472 (2013.01); B01J 23/866 (2013.01); B01J 23/92 (2013.01); B01J 23/94 (2013.01); B01J 38/02 (2013.01); C07C 5/42 (2013.01); C07C 2523/22 (2013.01); C07C 2523/26 (2013.01); C07C 2523/755 (2013.01); C07C 2523/847 (2013.01); C07C 2523/86 (2013.01)

(58) Field of Classification Search
None
See application file for complete search history.

(56) References Cited

U.S. PATENT DOCUMENTS

| 7,094,942 | B2 | 8/2006 | Abdulwahed et al. | |
|---|---|---|---|---|
| 2003/0171633 | A1* | 9/2003 | Xu | B01J 23/10 585/640 |
| 2004/0138051 | A1* | 7/2004 | Shan | B01J 23/26 502/60 |
| 2008/0200739 | A1* | 8/2008 | Walsdorff | C07C 5/3332 585/250 |
| 2009/0182186 | A1 | 7/2009 | Benderly et al. | |
| 2012/0083641 | A1 | 4/2012 | Ahmed et al. | |
| 2015/0209759 | A1 | 7/2015 | Ai-Hazmi et al. | |
| 2017/0151553 | A1 | 6/2017 | Lee et al. | |

* cited by examiner

Primary Examiner — Colin W. Slifka
(74) Attorney, Agent, or Firm — Maschoff Brennan

(57) ABSTRACT

The present invention relates to preparation of catalyst for production of olefinic hydrocarbons by dehydrogenation of their corresponding paraffins, particularly propylene from propane, comprising a metal oxide or combination of metal oxides utilizing spent catalyst from Fluid Catalytic Cracking (FCC)/Resid Fluid Catalytic Cracking (RFCC) processes. The metal oxides are possibly from transition metal group, particularly from groups VB, VIB, VIII, and Lanthanide series, and at least one metal from alkali group. The catalyst support used is spent catalyst or modified spent catalyst or combination thereof. The said catalyst can be used for both non-oxidative Propane Dehydrogenation (PDH) and Oxidative Propane Dehydrogenation (OPDH) process in the presence of $CO_2$.

13 Claims, No Drawings

CATALYST COMPOSITION FOR CONVERSION OF ALKANES TO ALKENES AND METHOD OF PREPARATION THEREOF

A catalyst composition for conversion of alkanes to alkenes and method of preparation thereof

FIELD OF THE INVENTION

This invention relates to a Catalyst and a process of production thereof, for production of olefinic hydrocarbons by dehydrogenation of their corresponding paraffins. The said catalyst can be used for both non-oxidative Propane Dehydrogenation (PDH) and Oxidative Propane Dehydrogenation (OPDH) process in the presence of $CO_2$.

BACKGROUND OF THE INVENTION

Conventional sources of propylene include Steam Cracking and Fluid Catalytic Cracking (FCC). Global demand for polypropylene has grown consistently in recently years. Due to the increased demand of propylene, alternative processes, such as, propane dehydrogenation has become prominent for on-purpose propylene production. Dehydrogenation is a chemical reaction where one or more hydrogen atoms are removed from a saturated molecule to produce an unsaturated compound. Oxidative dehydrogenation refers to a chemical reaction, wherein oxygen reacts with a hydrocarbon molecule to remove one or more hydrogen atoms from the hydrocarbon. This reaction requires an oxygen-containing gas or a gas mixture containing oxygen or oxygen on a carrier.

A typical propane dehydrogenation process involves an extensive use of alumina supported noble metal catalysts, such as, Pt/Al2O3, Pt—Sn/Al2O3 or alumina supported CrOx based catalysts.

U.S. Pat. No. 0,209,759A1 discloses a catalyst composition comprising (i) a porous metal oxide catalyst support, (ii) a precious metal, at least one of Pt, Pd, Rh, Re, Ru, Ir, (iii) Sn, (iv) Zn and/or (v) and alkaline earth metal. The catalyst is prepared by a process comprising (a) depositing the precious metal and/or on the porous metal oxide support to obtain a catalyst precursor, (b) subjecting the catalyst precursor to calcinations in an oxygen containing environment to obtain a catalyst, wherein the step (a) comprises the step (al) contacting the porous metal oxide catalyst support with a solution comprising a salt of the precious metals and a salt of Sn, Zn and or a salt of alkaline earth metal.

Another U.S. Pat. No. 0,151,553A1 describes a method of preparation of the catalyst comprising of metal (ZnO—$Al_2O_3$) alloy as carrier, and an active metal, and an auxiliary active metal, for dehydrogenation of $C_3$ and $C_4$ paraffins to their respective olefins by dehydrogenation. The active metal is claimed to be Pt and the auxiliary active metals are La and Sn.

Since propane dehydrogenation is an endothermic process with limited equilibrium, higher temperatures are required to achieve economically viable conversions. However, such high temperatures may lead to other side reactions, thereby decreasing the propylene selectivity, and accelerating catalyst deactivation. Oxygen promoted alkane dehydrogenation is exothermic, and therefore, can be carried out at lower temperatures.

U.S. Pat. No. 0,083,641A1 discloses a catalyst for oxidative dehydrogenation of propane to propylene, which includes vanadium and aluminium incorporated into the framework of mesoporous support to form V—Al-MCM-41, and nickel (5-15 wt %) impregnated onto the walls of the mesoporous support. The process includes carrying out the reaction in a fixed bed reactor, with feedstock as propane: oxygen:nitrogen ratio of about 6:6:88 by volume, at a temperature of 400 to 500° C. and atmospheric pressure, collecting the product, and separating propylene from the product. Propane conversion of 6-22% and propylene selectivity of 22-70% can be achieved from the claimed process.

Further, additional research was conducted to perform propane dehydrogenation in the presence of mild oxidants, such as, $CO_2$ in order to prevent excess oxidation occurring in the presence of 02. One such process is disclosed in U.S. Pat. No. 7,094,942B2, wherein the alkanes are converted to alkenes over Cr-based catalyst in the presence of $CO_2$ at a temperature in the range of about 400° C. to about 700° C., a pressure in the range of about 0.1 to 10 atm, wherein the alkane to $CO_2$ molar ratio is about 1:0.0001 to 1:0.045.

Another U.S. Pat. No. 0,182,186A1 describes a process for the conversion of propane to propylene, wherein a silica chromium catalyst is contacted with propane and $CO_2$. Further, the catalyst includes a promoter component (optionally) from V, Ag, Ce, Mo, Nz, Zr oxides and combination thereof.

For commercial production of propylene by propane dehydrogenation, one of the common feed sources is propane or propane rich feedstock ($C_3$ LPG) obtained as a product from FCC/RFCC processes. With the increase in demand for light olefins, gasoline, etc., over the years, the operating capacity of the FCC units worldwide has hugely increased, resulting in the generation of large amounts of spent catalyst. The spent catalysts cannot be disposed-off due to the stringent environmental regulations. The simplest solution thus is to re-use it in another process directly or by further modification.

Since spent RFCC catalysts contain metals such as, Ni, V, Fe, etc., which possess the ability to promote dehydrogenation of hydrocarbons, the spent RFCC catalysts can be directly used as catalysts for alkane dehydrogenation. Besides, suitable metals or metal oxides can be further added to the spent RFCC catalyst to form a mixed-metal catalyst, wherein the intrinsic metals (Ni, V, Fe) promote the dehydrogenation reaction along with the added active ingredients. The present invention describes the method for the preparation of catalyst for dehydrogenation of propane to propylene, utilizing cheaper sources, such as, spent catalyst from FCC/RFCC units, and non-precious metals or metal oxides as active components.

The disclosed method of preparation is applicable to spent catalysts from other processes, such as, Hydrodesulphurization, Catalytic reforming, Isomerisation, etc.

SUMMARY OF THE INVENTION

The primary objective of the present invention is to provide a Catalyst for production of olefinic hydrocarbons by dehydrogenation of their corresponding paraffins, particularly propylene from propane, comprising a metal oxide or combination of metal oxides supported on catalyst prepared using spent catalyst from Fluid Catalytic Cracking (FCC)/Resid Fluid Catalytic Cracking (RFCC) processes.

Another objective of the invention is to provide a profitable process for the utilization of spent catalysts from FCC/RFCC processes in the preparation of catalysts for conversion of alkanes to alkenes, preferably propane to propylene and iso-butane to iso-butene.

An embodiment of the present invention provides a process for production of a catalyst for dehydrogenation of alkanes to alkenes, the process comprising:
(a) obtaining spent catalyst from a refining process,
(b) calcining the spent catalyst to remove coke and/or any other volatile material,
(c) optionally grinding the spent catalyst to obtain spent catalyst support,
(d) providing a metal solution by mixing the desired metal containing compound (s) with a solvent,
(e) treating the spent catalyst or spent catalyst support with the metal solution to obtain a wet catalyst mixture or wet catalyst particles, drying the wet catalyst mixture or wet catalyst particles to obtain dry catalyst mixture or dry catalyst particles,
(g) optionally repeating the steps (e) and (f), and
(h) calcining the dry catalyst mixture or dry catalyst particles to obtain the catalyst.

Another embodiment of the present invention provides a process for production of a catalyst for dehydrogenation of alkanes to alkenes, the process comprising:
(a) obtaining spent catalyst from a refining process,
(b) calcining the spent catalyst to remove coke and/or any other volatile compounds,
(c) grinding the spent catalyst to obtain spent catalyst support,
(d) providing a binder gel by mixing binder alumina with dilute acid,
(e) providing a metal solution by mixing a metal containing compound with a solvent, treating the spent catalyst support with the binder gel and the metal solution to obtain catalyst particles, and
(g) calcining the catalyst particles to obtain the catalyst.

Yet another objective of the present invention is to provide a catalyst for dehydrogenation of alkanes to alkenes, wherein the catalyst comprises spent catalyst support; and 0.01 to 20 wt % of metals from group VB and/or VIB, or 0.01 to 5 wt % of group VIII metals, or 0.05 to 5 wt % of Lanthanide series; or a combination thereof.

DESCRIPTION OF THE INVENTION

While the invention is susceptible to various modifications and/or alternative processes and/or compositions, specific embodiment thereof has been shown by way of example in tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims.

The tables and protocols have been represented where appropriate by conventional representations, showing only those specific details that are pertinent to understanding the embodiments of the present invention so as not to obscure the disclosure with details that will be readily apparent to those of ordinary skill in the art having benefit of the description herein.

The following description is of exemplary embodiments only and is NOT intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

Any particular and all details set forth herein are used in the context of some embodiments and therefore should NOT be necessarily taken as limiting factors to the attached claims. The attached claims and their legal equivalents can be realized in the context of embodiments other than the ones used as illustrative examples in the description below.

According to a main embodiment, the present invention discloses a catalyst for production of olefinic hydrocarbons by dehydrogenation of their corresponding paraffin, particularly propylene from propane, comprising a metal oxide or combination of metal oxides utilizing spent catalyst.

The metal oxides are selected from transition metal group, more particularly from groups VB, VIB, VIII, and Lanthanide series, and at least one metal is selected from alkali group.

In accordance to an embodiment of the present invention, the catalyst support used may be selected from the spent catalyst or modified spent catalyst or combination thereof. The said catalyst may be used for both non-oxidative Propane Dehydrogenation (PDH) and Oxidative Propane Dehydrogenation (OPDH) process in the presence of $CO_2$. The refining process is selected from Fluid Catalytic Cracking (FCC) or Resid Fluid Catalytic Cracking (RFCC) processes or high severity fluid catalytic cracking process or high severity propylene maximizing fluid catalytic cracking process or hydro processing or isomerisation process or any other refinery process.

In accordance to detailed embodiment, the present invention provides a process for production of a catalyst for dehydrogenation of alkanes to alkenes, the process comprising:
(a) obtaining spent catalyst from a refining process,
(b) calcining the spent catalyst to remove coke and/or any other volatile material,
(c) optionally grinding the spent catalyst to obtain spent catalyst support,
(d) providing a metal solution by mixing the desired metal containing compound (s) with a solvent,
(e) treating the spent catalyst or spent catalyst support with the metal solution to obtain a wet catalyst mixture or wet catalyst particles,
(f) drying the wet catalyst mixture or wet catalyst particles to obtain dry catalyst mixture or dry catalyst particles,
(g) optionally repeating the steps (e) and (f), and
(h) calcining the dry catalyst mixture or dry catalyst particles to obtain the catalyst.

In accordance to a preferred embodiment of the present invention, there is also provided a process for production of a catalyst for dehydrogenation of alkanes to alkenes, the process comprising:
(a) obtaining spent catalyst from a refining process,
(b) calcining the spent catalyst to remove coke and/or any other volatile compounds,
(c) grinding the spent catalyst to obtain spent catalyst support,
(d) providing a binder gel by mixing binder alumina with dilute acid,
(e) providing a metal solution by mixing a metal containing compound with a solvent,
(f) treating the spent catalyst support with the binder gel and the metal solution to obtain catalyst particles, and
(g) calcining the catalyst particles to obtain the catalyst.

In accordance to another embodiment the present invention, treating of the spent catalyst support comprises of:
(i) mixing the binder gel with the spent catalyst support to obtain spent catalyst support slurry, (ii) drying the spent catalyst support slurry to obtain dry spent catalyst support cake,
(iii) crushing the dry spent catalyst support cake to obtain spent catalyst support particles,
(iv) treating the spent catalyst support particles with the metal solution to obtain wet catalyst particles,
(v) drying the wet catalyst particles to obtain catalyst particles, and
(vi) optionally repeating the steps (iv) and (v).

In accordance to yet another feature of the present invention, treating the spent catalyst support comprises:
(i) mixing the spent catalyst support, the binder gel and the metal solution to obtain catalyst slurry,
(ii) drying the catalyst slurry to obtain dry catalyst cake, and
(iii) crushing the dry catalyst cake to obtain catalyst particles.

In accordance to yet another feature of the present invention, treating the spent catalyst support comprises:
(i) mixing the spent catalyst support, the binder gel and the metal solution to obtain catalyst slurry,
(ii) spray drying of the catalyst slurry to obtain catalyst particles.

In accordance to a feature of the present invention, the process for dehydrogenation of alkanes to alkenes employing the catalyst obtained is carried out in the presence of an oxidizing agent, in particular carbon dioxide.

In accordance to another feature of the present invention, the catalyst mixture is dried at the desired temperature in the range of 100-150° C. In yet another feature of the present invention, the calcination is carried out at a temperature in the range of 500-650° C.

In accordance to another detailed embodiment, the present invention provides a catalyst composition to produce alkenes, particularly light olefins such as, propylene, butenes, etc. by dehydrogenation of their respective alkanes, wherein spent catalyst are used as catalyst support with metal oxides of transition group as active ingredients, particularly from groups VB, VIB VIII, and Lanthanide series, and at least one metal from alkali group.

In accordance to yet another feature of the present invention, the spent catalyst is used directly as catalyst to produce alkenes, particularly light olefins such as, propylene, butenes, etc. by dehydrogenation of their respective alkanes. In accordance to another feature of the present invention, the spent catalyst is obtained from the refining process, wherein the refining is selected from at least one of fluid catalytic cracking process, resid fluid catalytic cracking process, high severity fluid catalytic cracking process, high severity propylene maximizing fluid catalytic cracking process, hydro processing, isomerization process or any other refinery process.

In accordance to a feature of the present invention, the content of metals from group VB and VIB on the catalyst are in the range of 0.01-20 wt %. The content of the metals from group VIII and group IA on the catalyst are in the range of 0-5 wt %. The content of metals from Lanthanide series on the catalyst are in the range of 0.05-5 wt %.

In accordance to another feature of the present invention, the content of metals from group VB and VIB on the catalyst are preferably the range of 0.1-10 wt %. The contents of metal from group VIII and group IA on the catalyst are preferably in the range of 0.05-2 wt %. The content of metals from Lanthanide series on the catalyst are preferably in the range of 0.05-3 wt %.

In accordance to a feature of the present invention, the solvents are at least one of toluene and demineralized water (DM).

In accordance to a preferred embodiment of the present invention, the final catalyst obtained comprises metals from group VB and VIB in the range of 0.01-20 wt %, the metals from group VIII and group IA on the catalyst are in the range of 0-5 wt %. The content of metals from Lanthanide series on the catalyst are in the range of 0.05-5 wt %. and the alumina content in the range of 30-85 wt %.

In accordance to another preferred feature of the present invention, the final catalyst has surface area in the range of 20-200 m$^2$/g and apparent bulk densities (ABD) in the range of 0.6-1.10 g/cc.

In accordance to another embodiment of the present invention, there is provided a step of contacting the prepared final catalyst with feed stream containing light paraffins or mixture of paraffins and diluents, wherein the diluents could be $CO_2$, $N_2$, steam, inert gas, flue gas or combination thereof, is carried out at a temperature in the range of 500-700° C., pressure in the range of 0.01 to 10 bar and GHSV in the range of 500-3000 in at least one of fixed bed, fluidized bed, moving bed reactor, and a combination thereof. The ratio of alkane to diluent or mixture of diluents is in the range of 1:0.1 to 1:10. The conversion of light paraffins is achieved in the range of 15-55 wt % with the selectivity of light olefin in the range of 25-90 wt %.

In accordance to yet another embodiment of the present invention, the spent catalyst from RFCC unit which is used in the following examples was calcined at 593° C. (ramp rate of 3.5° C./min) for 3 hours to remove carbon deposits. The calcined catalyst herein after termed as 'Catalyst support'. The typical physical properties of the catalyst support are indicated in Table 1. The performance of the catalyst support was evaluated for OPDH and PDH processes according to the method presented in Examples 6 and 7 respectively.

TABLE 1

| Physico-chemical properties of the catalyst support | | | |
|---|---|---|---|
| SA (m2/g) | PV (cc/g) | ABD (g/cc) | Metal content (wt %) |
| 133 | 0.249 | 0.896 | $Al_2O_3$: 41.2 |
| | | | Ni: 0.47 |
| | | | V: 0.53 |
| | | | Na: 0.27 |
| | | | $RE_2O_3$: 2.40 |
| | | | Fe: 0.22 |

The present invention is exemplified by, but not limited to the following examples.

Example 1

Preparation of Dehydrogenation Catalyst by Impregnation of V and Ni on Catalyst Support:

For enhancing the propylene yield and selectivity in both oxidative and non-oxidative PDH processes, the amount of intrinsic metals of the said catalyst support, Vanadium and Nickel, was increased to desired value by doping additional V and Ni by wet-impregnation method, as described below.
(i) 12.8 g of Vanadium Octoate (containing 3.63 wt % V) and 1.168 g of nickel octoate (containing 7.86 wt % Ni) were mixed together and the mixture was diluted with 5 mL of toluene (solvent).
(ii) The solution was then added drop wise to 50 g of above catalyst support with continuous stirring, till the catalyst became wet, i.e., till its pores were completely filled.

(iii) The catalyst was then dried on a hot plate to remove the solvent.
(iv) Steps (ii) and (iii) were repeated till the solution containing metals was exhausted.
(v) The catalyst was then calcined at 593° C. (ramp rate of 3.5° C./min) for 1 hour in presence of air.
(vi) The steps (i) to (v) were repeated further for three times, and the catalyst calcination for the fourth time was carried out at 593° C. (ramp rate of 3.5° C./min) for 3 hours in air.

Thus prepared catalyst was labeled as Cat-1A, and its physico-chemical properties are indicated in table 2. The performance of the Cat-1A was tested according to the method presented in Example 6. Cat-1B was prepared by subjecting Cat-1A to reduction in a fixed bed/fixed-fluidized bed reactor using Hydrogen gas, at 600-800° C. at a controlled flow rate. The performance of the Cat-1B was evaluated as per the method presented in Example 7.

Example 2

Preparation of Dehydrogenation Catalyst by Impregnation of V on Catalyst Support:

The active metal component, Vanadium, was doped on the said catalyst support by wet-impregnation method as described below.
(i) 15.2 g of Vanadium Octoate (containing 3.63 wt % V) was taken in a beaker and diluted with 5 mL of toluene (solvent).
(ii) The solution was then added drop wise to 50 g of catalyst support with continuous stirring, till the catalyst became wet, i.e., till its pores were completely filled.
(iii) The catalyst was then dried on a hot plate to remove the solvent.
(iv) Steps (ii) and (iii) were repeated till the solution containing metal was exhausted.
(v) The catalyst was then calcined at 593° C. (ramp rate of 3.5° C./min) for 1 hour in presence of air.
(vi) The steps (i) to (v) were repeated further for three times, and the catalyst calcination for the fourth time was carried out at 593° C. (ramp rate of 3.5° C./min) for 3 hours in presence of air.

Thus prepared catalyst was labeled as Cat-2A, and its physico-chemical properties are indicated in table 2. The performance of the Cat-2A was tested according to the method presented in Example 6. Cat-2B was prepared by subjecting Cat-1A to reduction in a fixed bed/fixed-fluidized bed reactor using Hydrogen gas, at 600-800° C. at a controlled flow rate. The performance of the Cat-2B was evaluated as per the method presented in Example 7.

Example 3

Preparation of Dehydrogenation Catalyst by Impregnation of Cr and Ni on Catalyst Support:

The active ingredients, Chromium and Nickel, were doped on the said catalyst support by wet-impregnation method as described below.
(i) 13.6 g of Chromium nitrate nonahydrate (97% purity) was dissolved in 15.7 mL of DM water (solvent) and taken in a burette.
(ii) The solution was added drop wise to 50 g of catalyst support with continuous stirring, till the catalyst became wet, i.e., till its pores were completely filled.
(iii) The catalyst was then dried on a hot plate to remove the solvent.
(iv) Steps (ii) and (iii) were repeated till the solution containing Cr was exhausted.
(v) The catalyst was then calcined at 593° C. (ramp rate of 3.5° C./min) for 1 hour in the presence of air.
(vi) 1.45 g of nickel octoate (containing 7.86 wt % Ni) was taken and diluted with 10 mL of toluene (solvent).
(vii) The solution containing nickel was then added drop wise to the catalyst obtained from step (v) under continuous stirring, till the catalyst became wet, i.e., till its pores were completely filled.
(viii) The catalyst was then dried on a hot plate to remove the solvent.
(ix) Steps (vii) and (viii) were repeated till the solution containing Ni was exhausted.
(x) The catalyst was finally calcined at 593° C. (ramp rate of 3.5° C./min) for 3 hour in the presence of air.

Thus prepared catalyst was labeled as Cat-3A, and its physico-chemical properties are indicated in table 2. The performance of the Cat-3A was tested according to the method presented in Example 6. Cat-3B was prepared by subjecting Cat-3A to reduction in a fixed bed/fixed-fluidized bed reactor using Hydrogen gas, at 600-800° C. at a controlled flow rate. The performance of the Cat-3B was evaluated as per the method presented in Example 7.

Example 4

Preparation of Dehydrogenation Catalyst by Impregnation of Cr and K on Modified Catalyst Support:

To prepare the modified catalyst support, 35 g of spent RFCC catalyst having properties as listed in table 1, and 11.6 g of binder alumina (on dry basis) were taken.
(i) The said spent catalyst was subjected to wet grinding till the particles of size <5 microns were obtained.
(ii) 55 mL of formic acid solution (containing 10 vol % HCOOH in distilled water) was taken in a beaker and kept under continuous stirring.
(iii) Measured amount of binder alumina was added to the beaker and allowed to mix for 15-20 mins to form a gel. The prepared gel was further aged for 15-20 minutes.
(iv) The grinded paste of catalyst support obtained from step (i) was then added to the alumina gel under continuous stirring to make homogenous catalyst slurry (60 mL of water was gradually added to prevent the formation of lumps and maintain the consistency/flow ability).
(v) The catalyst slurry was dried in oven at 120° C. for 16 hours to get a dry cake of catalyst.
(vi) The dried cake was crushed and sieved to obtain particles of 0.5-1.0 mm, as suitable for fixed bed operation. Alternatively, the catalyst can be crushed and sieved to get particles of 20-200 microns for fluidized bed operation.
(vii) The catalyst was then calcined at 593° C. (ramp rate of 3.5° C./min) for 3 hours. Thus obtained catalyst was labeled as Cat-X.
(viii) 11.8 g of Chromium nitrate nonahydrate (98% purity) and 0.41 g of anhydrous Potassium nitrate (99% purity) were dissolved together in 7.5 mL of DM water.
(ix) The solution was then added drop wise to 20 g of cat-X under continuous stirring, till the catalyst became wet, i.e., till its pores were completely filled.
(x) The catalyst was then dried on a hot plate.
(xi) Steps (x) and (xi) were repeated till the solution containing metals was exhausted.
(xii) The catalyst was then calcined at 550° C. (ramp rate of 3.0° C./min) for 3 hour in presence of air.

Thus prepared catalyst was labeled as Cat-4A, and its physic-chemical properties are indicated in Table 2. The performance of the Cat-4A was tested according to the method presented in Example 6. Cat-4B was prepared by subjecting Cat-4A to reduction in a fixed bed/fixed-fluidized bed reactor using Hydrogen gas, at 600-800° C. at a controlled flow rate. The performance of the Cat-4B was evaluated as per the method presented in Example 7.

Example 5

Preparation of Dehydrogenation Catalyst Containing Cr, K and Modified Catalyst Support:

To prepare the dehydrogenation catalyst, 35 g of catalyst support having properties as listed in table 1, and 27 g of binder alumina (on dry basis) were taken.
  (i) The said catalyst support was subjected to wet grinding till the particles of size <5 microns were obtained.
  (ii) 65 mL of formic acid solution (containing 10 vol % HCOOH in distilled water) was taken in a beaker and kept under continuous stirring.
  (iii) Measured amount of binder alumina was added to the beaker and allowed to mix for 15-20 mins to form a gel. The prepared gel was further aged for 15-20 minutes.
  (iv) Simultaneously, 29.5 g of Chromium nitrate nonahydrate (98% purity) and 0.95 g of anhydrous Potassium nitrate (99% purity) were dissolved together in 15 mL of DM water.
  (v) The grinded paste of catalyst support obtained from step (i) and the metal solution were then added to the alumina gel under continuous stirring to make homogenous catalyst slurry (50 mL of water was gradually added to prevent the formation of lumps and maintain the consistency/flow ability).
  (vi) The catalyst slurry was dried in oven at 120° C. for 16 hours to get a dry cake of catalyst.
  (vii) The dried cake was crushed and sieved to obtain particles of 0.5-1.0 mm, as suitable for fixed bed operation. Alternatively, the catalyst can be crushed and sieved to get particles of 20-200 microns for fluidized bed operation.
  (viii) The catalyst was then calcined at 550° C. (ramp rate of 3.0° C./min) for 3 hour in presence of air.

Thus prepared catalyst was labeled as Cat-5A, and its physico-chemical properties are indicated in Table 2. The performance of the Cat-5A was tested according to the method presented in Example 6. Cat-5B was prepared by subjecting Cat-5A to reduction in a fixed bed/fixed-fluidized bed reactor using Hydrogen gas, at 600-800° C. at a controlled flow rate. The performance of the Cat-5B was evaluated as per the method presented in Example 7.

TABLE 2

Physico-chemical properties of the catalysts prepared using spent RFCC catalyst

| Catalyst | SA (m2/g) | ABD (g/cc) | Alumina content (wt %) | Metal concentration (wt %) |
|---|---|---|---|---|
| Cat-1A | 37.7 | 1.05 | 39.2 | V: 3.9; Ni: 1.05 |
| Cat-2A | 27.1 | 1.01 | 39.2 | V: 4.4; Ni: 0.33 |
| Cat-3A | 121 | 1.08 | 39.5 | Cr: 3.1; Ni: 0.65; V: 0.46 |
| Cat-4A | 137 | 0.738 | 54.2 | Cr: 6.34; K: 0.69; V: 0.39; Ni: 0.25 |
| Cat-5A | 172 | 0.703 | 65.7 | Cr: 5.58; K: 0.52; V: 0.26; Ni: 0.25 |

Example 6

Performance Evaluation of Catalysts for Oxidative Propane Dehydrogenation Process The performance of the catalysts, Cat-1A, Cat-2A, Cat-3A, Cat-4A, Cat-5A and catalyst support was evaluated using a fixed-bed tubular reactor of 9 mm ID containing 1-2 g catalyst at reaction temperature of 650° C., as measured by the thermocouple located in the catalyst bed. The feed stream contained propane, CO2 and N2 in the molar ratio of C3:CO2:N2=26:53:21 and Gas hourly space velocity (GHSV) of the feed gas was 1500-2000 $h^{-1}$. The flow rates of inlet gases were controlled by mass flow controllers. The inlet and outlet gas compositions were analyzed in a Refinery Gas Analyzer equipped with TCD and FID at regular intervals. Propane conversion, propylene yield and selectivity were calculated using the following formula, and the obtained results are summarized in Table-3. The data shown in Table-3 is calculated based on the product composition at 20 minutes after the start of the run.

$$\% \text{ Conversion} = \frac{\text{weight of propane (in)} - \text{weight of propane (out)}}{\text{weight of propane (in)}} * 100$$

$$\% \text{ Yield} = \frac{\text{weight of propylene formed}}{\text{weight of propane (in)}} * 100$$

$$\% \text{ Selectivity} = \frac{\text{Propylene yield}}{\text{Propane conversion}} * 100$$

TABLE 3

Catalyst activity test results of prepared catalysts for Oxidative PDH process

| Catalyst | Propane conversion (wt %) | Propylene yield (wt %) | Propylene selectivity (wt %) |
|---|---|---|---|
| Catalyst support | 17.1 | 6.4 | 37.5 |
| Cat-1A | 20.7 | 10.9 | 52.7 |
| Cat-2A | 15.4 | 9.6 | 62 |
| Cat-3A | 22.8 | 12 | 52.8 |
| Cat-4A | 30.2 | 20.7 | 68.6 |
| Cat-5A | 41.9 | 22.1 | 52.8 |

Example 7

Performance Evaluation of Catalysts for Non-Oxidative Propane Dehydrogenation Process The performance of the catalysts, Cat-1B, Cat-2B, Cat-3B, Cat-4B, Cat-5B and catalyst support was evaluated using a fixed-bed tubular reactor of 9 mm ID containing 1-2 g catalyst at reaction temperature of 630-700° C., as measured by the thermocouple located in the catalyst bed. The feed stream contained propane and N2 in the molar ratio of C3:N2=1:2 and Gas hourly space velocity (GHSV) of the feed gas was 2200-3000 $h^{-1}$. The flow rates of inlet gases were controlled by mass flow controllers. The inlet and outlet gas compositions were analyzed in a Refinery Gas Analyzer equipped with TCD and FID at regular intervals. Propane conversion, propylene yield and selectivity were calculated using the formulae as given in example 6, and the obtained results are summarized in Table 4. The data shown in Table-4 is calculated based on the product composition at 20 minutes after the start of the run.

TABLE 4

Catalyst activity test results of prepared
catalysts for non-oxidative PDH process

| Catalyst | Propane conversion (wt %) | Propylene yield (wt %) | Propylene selectivity (wt %) |
|---|---|---|---|
| Catalyst support* | 51 | 15.2 | 29.7 |
| Cat-1B | 43.7 | 12.5 | 28.6 |
| Cat-2B | 40.8 | 14.2 | 34.4 |
| Cat-3B | 39.4 | 13 | 33.2 |
| Cat-4B | 43.4 | 33.6 | 77.3 |
| Cat-5B | 41 | 34.1 | 83.1 |

*The catalyst support is pre-treated with $H_2$ similar to Examples 1-5 prior to reaction The invention will be fully and particularly described in this complete patent application.

The invention claimed is:

1. A process for production of a catalyst for dehydrogenation of alkanes to alkenes, the process comprising:
    (a) obtaining spent catalyst from a refining process;
    (b) calcining the spent catalyst to remove coke and/or any other volatile material;
    (c) optionally grinding the spent catalyst to obtain spent catalyst support;
    (d) providing a metal solution by mixing metals containing compounds with a solvent;
    (e) treating the spent catalyst or spent catalyst support with the metal solution to obtain a wet catalyst mixture or wet catalyst particles;
    (f) drying the wet catalyst mixture or wet catalyst particles to obtain dry catalyst mixture or dry catalyst particles;
    (g) optionally, repeating the steps (e) and (f); and
    (h) calcining the dry catalyst mixture or dry catalyst particles to obtain the catalyst;
    wherein the refining process is fluid catalytic cracking process, resid fluid catalytic cracking process, high severity fluid catalytic cracking process, high severity propylene maximizing fluid catalytic cracking process, hydro processing or isomerisation process.

2. The process according to claim 1, wherein the metals in the metals containing compounds are selected at least one metal from groups, VB, VIB, VIII, and Lanthanide series, and at least one metal is from alkali group metals.

3. The process according to claim 1, wherein the drying is carried out at a temperature in the range of 100-150° C.

4. The process according to claim 1, wherein calcining is carried out at a temperature in the range of 500-650° C.

5. The process according to claim 1, wherein the solvent is toluene or demineralized water (DM) or a combination thereof.

6. A process for production of a catalyst for dehydrogenation of alkanes to alkenes, the process comprising:
    (a) obtaining spent catalyst from a refining process;
    (b) calcining the spent catalyst to remove coke and/or any other volatile compounds;
    (c) grinding the spent catalyst to obtain spent catalyst support;
    (d) providing a binder gel by mixing binder alumina with dilute acid;
    (e) providing a metal solution by mixing metals containing compounds with a solvent;
    (f) treating the spent catalyst support with the binder gel and the metal solution to obtain catalyst particles; and
    (g) calcining the catalyst particles to obtain the catalyst;
    wherein the refining process is fluid catalytic cracking process, resid fluid catalytic cracking process, high severity fluid catalytic cracking process, high severity propylene maximizing fluid catalytic cracking process, hydro processing or isomerisation process.

7. The process according to claim 6, wherein treating the spent catalyst support comprises:
    (i) mixing the binder gel with the spent catalyst support to obtain spent catalyst support slurry;
    (ii) drying the spent catalyst support slurry to obtain dry spent catalyst support cake;
    (iii) crushing the dry spent catalyst support cake to obtain spent catalyst support particles;
    (iv) treating the spent catalyst support particles with the metal solution to obtain wet catalyst particles;
    (v) drying the wet catalyst particles to obtain catalyst particles; and
    (vi) optionally repeating the steps (iv) and (v).

8. The process according to claim 6, wherein treating the spent catalyst support comprises:
    mixing the spent catalyst support, the binder gel and the metal solution to obtain catalyst slurry;
    (ii) drying the catalyst slurry to obtain dry catalyst cake; and
    (iii) crushing the dry catalyst cake to obtain catalyst particles.

9. The process according to claim 6, wherein treating the spent catalyst support comprises:
    (i) mixing the spent catalyst support, the binder gel and the metal solution to obtain catalyst slurry; and
    (ii) Spray drying of the catalyst slurry to obtain catalyst particles.

10. The process according to claim 6, wherein the metals in the metals containing compounds are selected at least one metal from groups, VB, VIB, VIII and Lanthanide series, and at least one metal is from alkali group metals.

11. The process according to claim 6, wherein the drying is carried out at a temperature in the range of 100-150° C.

12. The process according to claim 6, wherein calcining is carried out at a temperature in the range of 500-650° C.

13. The process according to claim 6, wherein the solvent is toluene or demineralized water (DM) or a combination thereof.

* * * * *